United States Patent [19]
Carden

[11] Patent Number: 5,980,602
[45] Date of Patent: Nov. 9, 1999

[54] METAL MATRIX COMPOSITE

[75] Inventor: Robin A. Carden, Costa Mesa, Calif.

[73] Assignee: Alyn Corporation, Irvine, Calif.

[21] Appl. No.: 08/836,010

[22] PCT Filed: May 2, 1996

[86] PCT No.: PCT/US96/06176

§ 371 Date: May 6, 1997

§ 102(e) Date: May 6, 1997

[87] PCT Pub. No.: WO97/13600

PCT Pub. Date: Apr. 17, 1997

Related U.S. Application Data

[60] Continuation-in-part of application No. 08/536,695, Sep. 29, 1995, which is a division of application No. 08/183,728, Jan. 19, 1994, Pat. No. 5,486,223.

[51] Int. Cl.$^6$ .................................................. B22F 3/10
[52] U.S. Cl. ........................... 75/236; 75/249; 419/17; 419/38; 419/41; 419/45; 419/54
[58] Field of Search ........................ 419/17, 38, 41, 419/45, 54; 75/236, 249

[56] References Cited

U.S. PATENT DOCUMENTS

| | | |
|---|---|---|
| 3,178,807 | 4/1965 | Bergmann . |
| 3,591,362 | 7/1971 | Benjamin . |
| 4,104,062 | 8/1978 | Weaver . |
| 4,605,440 | 8/1986 | Halverson et al. . |
| 4,623,388 | 11/1986 | Jatkar et al. . |
| 4,661,154 | 4/1987 | Faure . |
| 4,702,770 | 10/1987 | Pyzik et al. . |
| 4,749,545 | 6/1988 | Begg et al. . |
| 4,793,967 | 12/1988 | Pryor et al. . |
| 4,894,088 | 1/1990 | Yamaguchi et al. . |
| 4,941,918 | 7/1990 | Horikoshi et al. . |
| 4,943,320 | 7/1990 | Pechnik et al. . |
| 4,946,500 | 8/1990 | Zedalis et al. . |
| 4,961,778 | 10/1990 | Pyzik et al. . |
| 4,981,643 | 1/1991 | Siemers et al. . |
| 5,006,417 | 4/1991 | Jackson et al. . |
| 5,034,282 | 7/1991 | Hribernik et al. . |
| 5,039,633 | 8/1991 | Pyzik et al. . |
| 5,045,278 | 9/1991 | Das et al. . |
| 5,114,505 | 5/1992 | Mirchandani et al. . |
| 5,128,213 | 7/1992 | Tanaka et al. . |
| 5,273,569 | 12/1993 | Gilman et al. . |
| 5,372,775 | 12/1994 | Hayashi et al. . |
| 5,401,338 | 3/1995 | Lin . |
| 5,435,825 | 7/1995 | Kusui et al. . |

OTHER PUBLICATIONS

"Powder Techniques in Processing of Metal Matrix Composites" by H.J. Rack in *Metal Matrix Composites: Processing and Interfaces* edited by R.K. Everett and R.J. Arsenault, Academic Press, 1991, pp. 83–101.

*Primary Examiner*—Daniel J. Jenkins
*Attorney, Agent, or Firm*—Cooper & Dunham LLP

[57] ABSTRACT

An improved metal matrix composite utilizes boron carbide as a ceramic additive to a base material metal. The base material metal is aluminum, magnesium, or titanium, or an alloy thereof, provided in powder form with the balance of the material comprising various trace metals such as chromium, copper, iron, magnesium, silicon, titanium, and zinc. The boron carbide powder comprises 10 to 30% by weight of the metal matrix composition. There is at least one other metal additive. The compositions are useful in a variety of applications where lightweight, strength, stiffness, hardness, and low density are desirable. The compositions are extrudable and weldable.

15 Claims, No Drawings

METAL MATRIX COMPOSITE

CROSS-REFERENCE

This is a continuation-in-part of application Ser. No. 08/536,695, filed Sep. 29, 1995, which, in turn, is a division of application Ser. No. 08/183,728, filed Jan. 19, 1994, now U.S. Pat. No. 5,486,223.

BACKGROUND OF THE INVENTION

1. Field of the Invention

The present invention relates generally to metal matrix compositions. Such compositions or composites comprise one or more base material metals such as, for example, aluminum, titanium, or magnesium, to which is added a selected percentage of ceramic material to alter the properties of the base material metal(s) in a positive manner. Strength, hardness, and drawability are increased. Drawability facilitates fabrication of various articles of manufacture from such composite materials. More specifically, the present invention pertains to an improved metal matrix composite which, in a preferred embodiment, uses boron carbide as the added ceramic material. The composites result from a novel method of manufacture producing a composite which is lighter, stronger, stiffer, and which has a higher fatigue strength than other available alloys of the base material metal, and which is also lighter, stronger, stiffer, and which has a higher fatigue strength than prior art metal matrices, composites, and particularly those metal matrix composites which are of comparable cost.

2. Prior Art

In recent years metal matrix compositions or composites have become popular materials for a variety of applications. This new family of materials has become popular because of improvements in stiffness, strength, and wear properties. Basic metal matrix composites are made typically with aluminum, titanium, or magnesium as the base material metal. Then certain percentages of ceramics are added. Typical ceramics include boron carbide, silicon carbide, titanium diboride, titanium carbide, aluminum oxide, and silicon nitride. Most known metal matrix composites are made by introducing the ceramics into the molten metal. In large production runs of metal matrix composites, the ceramic reinforcement must be wetted by the liquid metal to facilitate incorporation of the reinforcement into the melt. In those metal matrix composites using silicon carbide and aluminum, the silicon carbide is thermodynamically unstable in molten aluminum which leads to the formation of aluminum carbide at the interface and increased concentration of silicon in the material matrix during the solidification process. This interface reaction is believed to have detrimental effects on the mechanical properties of the resulting composite by reducing the interface strength and changing the composition.

Recently, powder metallurgy consolidation has emerged as a competing method of fabricating metal matrix composites by consolidating the powders by means of hot pressing and conventional powder metallurgy operations with vacuum sintering used to achieve a high density green body. By following certain isopressing and sintering techniques, a 99% theoretical density billet can be achieved.

In the present invention, it has been found that the most desirable ceramic candidate for metal matrix composites is boron carbide. Boron carbide is the third hardest material known and the hardest material produced in tonnage. Boron carbide powders can be formed by a variety of reactions including the carbon reduction of any of several boron-oxygen compounds including boric oxide, borax, boracite, as well as by the direct combination of the elements. Usually, most commercial boron carbide is produced in arc furnaces. Boric acid is added together with carbon in the form of coke and heated to very high temperatures. An electric arc is maintained between graphite electrodes inside a furnace. The synthesis reaction is accompanied by the release of large volumes of carbon monoxide. Venting and disposal of the carbon monoxide gas constitutes a major design consideration. Boron carbide is also the lightest of the ceramics typically used in metal matrix composite technology, but it is very hard and expensive. Its hardness limits its extrudability. Thus it would be highly advantageous if it were possible to produce an improved metal matrix composite which utilizes an advanced ceramic such as boron carbide but which, unlike the prior art, results in an extrudable composite material that allows easy fabrication of various articles of manufacture so that such resulting articles have the specific strength and stiffness improvements as compared to equivalent articles of manufacture using only the base material metals.

SUMMARY OF THE INVENTION

The present invention comprises an improved metal matrix composite which, in a preferred embodiment disclosed herein, utilizes boron carbide as the ceramic additive to a base material metal. The fabrication process is unlike that of a number of other metal matrix composites because it is not made through molten processes. More specifically, instead of melting the boron carbide with the aluminum, nickel, zinc, magnesium, titanium, or other base material metal, the metal matrix composite of the present invention begins with the blending of powders of all the various elements such as by means of a jet mill which is basically an air blaster used to uniformly mix powdered substances and avoid stratification and settling. After the particles have been sufficiently mixed, they are directed into a die and then into a cylindrical container where the particulates are subjected to extremely high pressures transforming the elements into a solid ingot. It is from these ingots that the extrusion tubes or other articles of manufacture may then be made. The resulting advanced metal matrix composites of the boron carbide embodiment of the invention are 60% lighter, 30% stronger, 40–45% stiffer, and 50% higher in fatigue strength than any of the top of the line 7000 series aluminum alloy materials. In addition, the inventive material is 7–8% lighter, 26% stronger, 5% stiffer, and has 35–40% greater fatigue strength than most popular metal matrix composites available in the prior art.

In one embodiment disclosed herein, the base material metal is preferably aluminum, magnesium, or titanium, or an alloy thereof, provided in powder form and preferably being approximately 97% pure, with the balance of the material comprising various trace metals such as chromium, copper, iron, magnesium, silicon, titanium, and zinc. The boron carbide powder is 99.5% pure boron carbide having a particulate size in the range of 2–19 microns with a mean or average size of approximately 8.4 microns. In one typical embodiment of the invention, the metal base material was selected from an aluminum alloy 6061T-6 to which was added approximately 12% by weight the aforementioned boron carbide powder to which was added silicon in an amount of 0.1–0.4%, iron in the amount of 0.05–0.4%, and aluminum in the amount of 0.05–0.4%. There is at least one other metal additive. The underlying boron carbide material was approximately 77% boron content and 22% carbon content.

A metal matrix composite made from the aforementioned materials in accordance with the fabrication process of the present invention to be described hereinafter, typically may result in a composite material which exhibits a tensile strength of about 62–108 kpsi, a yield strength of about 58–97 kpsi, and a modulus of elasticity of about 14.25–14.50 Mpsi. Furthermore, the resulting material is approximately as hard as chromoly steel but has a density which is even lower than aluminum alloy.

Importantly, the material of the present invention is readily extrudable. Ingots of the metal matrix composites of the present invention are extruded through a titanium diboride die bearing material which exhibits a significant increase in die insert life. The die bearing material alternatively may be tungsten carbide, tungsten carbide composite, boron carbide, carbon nitride, a plasma vapor deposited ceramic such as titanium carbide or a chemically deposited ceramic such as titanium nitride. Furthermore, the present invention is readily weldable. In fact, the coated boron carbide particulates of the material disclosed herein tend to flux and move into the weld pool which creates a very strong weld joint. Thus the present invention is not only highly suited for the manufacture of various shaped articles, but is also suited for interconnecting such articles by conventional welding processes as will be hereinafter more fully explained.

OBJECTS OF THE INVENTION

It is therefore a principal object of the present invention to provide an improved metal matrix composite material which exhibits certain advantageous properties and manufacturability conducive to the fabrication of certain articles of manufacture having improved characteristics such as reduced weight, higher strength, and increased hardness.

It is an additional object of the present invention to provide an improved metal matrix composite material which is especially adapted for use as structural members in lightweight applications such as bicycle frames and the like while retaining or improving the strength and hardness at the same or lower relative cost of comparable materials used in similar structures.

It is still an additional object of the present invention to provide a metal matrix composite material which is stiffer and lighter than aluminum while being comparable in hardness to steel and extremely fracture resistant while also being extrudable and weldable, thus permitting the fabrication of extremely high strength, lightweight structural members at reasonable cost.

It is still an additional object of the present invention to provide a method for manufacturing an improved metal matrix composite material to result in a material having superior hardness, strength, and density characteristics while being extrudable and weldable for use in the manufacture of a variety of structural members which may be readily connected to one another such as in bicycle and other vehicle frames and components, engine components, aircraft parts, tooling, sporting equipment such as tennis rackets, badminton rackets, baseball bats, arrows, golf club shafts, and hockey and lacrosse sticks, eyewear, automotive parts, electronic parts, furniture, medical equipment, battery housings, nuclear shielding, marine components, robots, carts and seats, gourmet cookware, toy casings, high-pressure containers, tank linings, and armor, for example.

DETAILED DESCRIPTION OF PREFERRED EMBODIMENTS

One preferred embodiment of the present invention uses aluminum alloy as a base material metal and boron carbide as the added ceramic material. In a preferred embodiment of manufacture the aluminum alloy is provided in the form of a metal powder which is blended with jet milled boron carbide particulates that have been processed and have certain chemical and particulate size attributes. The boron carbide is preferably at least 99.5% pure and has a 2–19 micron particle size with an average particle size of about 8.4 microns. Included in the boron carbide powder is 0.1–0.4% silicon, 0.05–0.4% iron, and 0.05–0.4% aluminum. Trace amounts of magnesium, titanium, and calcium may also be provided. Two exemplary semi-quantitative analyses of acceptable boron carbide powders for use in the present invention are shown hereinbelow in Tables I and II.

TABLE I

| | |
|---|---|
| B | 77.3% |
| Si | 0.37 |
| Mg | 0.0016 |
| Fe | 0.026 |
| Al | 0.18 |
| Cu | 0.0021 |
| Ti | 0.0088 |
| Ca | 0.0049 |
| other elements | (nil) |
| C, $O_2$ | (bal) |

TABLE II

| | |
|---|---|
| B | 77.7% |
| Si | 0.14 |
| Mg | 0.0017 |
| Fe | 0.074 |
| Al | 0.13 |
| Cu | ND 0.0002 |
| Ti | 0.017 |
| Ca | 0.0048 |
| other elements | (nil) |
| C, $O_2$ | (bal) |

The addition of small amounts of pure aluminum, silicon, and iron to the arc furnace during the production of boron carbide, such as by the reaction of boric acid and carbon, has been found to improve the boron carbide for use in this metal matrix composite. These elements are usually present in an amount less than 3.0% by weight. These metal elements do not go out of solution. They stay in the boron carbide and provide a chelating opportunity for the base material aluminum. These additional metals form an intermetallic chemical bond with the main metal alloy. However, it will be understood that the aforementioned additions of pure aluminum, silicon, and iron, may not be the only metals which can be used for the aforementioned purpose. By way of example, virtually any low temperature reacting metal that forms an intermetallic phase below the processing temperature of the metal matrix composite ingot would be usable in the present invention for the purpose indicated.

A typical relative weight contribution of the boron carbide powder and base material metal powder is 10–30% of the former and 70–90% of the latter depending upon the specific characteristics desired for the finished product. Several typical formulations are as follows:

1. A metal matrix composite of aluminum alloy 6061 base metal material and 20 weight % boron carbide. This composite material is extrudable and exhibits a tensile strength of 65.3 kpsi and a yield strength of 59.8 kpsi. It is useful for structural components for transportation vehicles and computer discs. It has stiffness and strength.

2. A metal matrix composite of aluminum alloy 6061 base metal material and 25 weight % boron carbide. This composite material is extrudable and exhibits a tensile strength of 71.9 kpsi and a yield strength of 62.6 kpsi. This formulation is useful for brake discs and marine castings. It has corrosion resistance and wearability.

3. A metal matrix composite of aluminum alloy 6061 base metal material and 30 weight % boron carbide. This composite material is extrudable and exhibits a tensile strength of 62.3 kpsi and a yield strength of 58.4 kpsi. The formulation may be used for structural stiffness for marine applications or nuclear shielding since it has strength and corrosion resistance.

4. A metal matrix composite containing aluminum alloy 7091 base metal material and 20 weight % boron carbide. This composite material exhibits a tensile strength of 98.6 kpsi, a yield strength of 89.2 kpsi, and is extrudable. This composition has utility for spacecraft and satellites. It has low thermal expansion and high tensile strength.

5. A metal matrix composite containing aluminum alloy 7091 base metal material and 30 weight % boron carbide. This composite material exhibits a tensile strength of 107.9 kpsi, a yield strength of 96.4 kpsi, and is extrudable. The material is useful for containers for high pressure and corrosive materials. The material has high strength and corrosion resistance.

After the boron carbide has been jet milled to the selected particulate size and with the aluminum alloy powder blended together in a double chamber "V" blender, for two and one-half hours at 20 to 30 RPM in an inert gas, the powders are degassed at 200 degrees Centigrade for one hour in a vacuum of 5 to 8 Torr and then placed in a latex bag and isopressed at 65,000 psi. The isopress bag resembles the shape of the ingot that is to be extruded. The latex bag is degassed and clamped off. The maximum pressure is held for at least a one minute soak. The resulting ingots are removed from the bag and placed into a vacuum furnace to undergo a sintering cycle in accordance with the following preferred embodiment of the process of the present invention.

First, the ingots are heated from room temperature to 300 degrees Centigrade over a twenty minute ramp period during which time binder and water are burned off. The ingots are then heated to 450 degrees Centigrade over a fifteen minute ramp period during which the remaining binder is burned off. The ingots are then heated to 625 degrees Centigrade over a forty minute ramp period during which the temperature increases accordingly. At 625 degrees Centigrade the ingot is held and soaked at that temperature for 45 minutes during which close grain boundaries are formed. The ingot is then cooled from 625 degrees Centigrade to 450 degrees Centigrade over a twenty minute period by means of a nitrogen gas backfill. Finally, the ingots are cooled to room temperature at a rate not faster than 40 degrees Centigrade per minute again using nitrogen gas. The ingots are then turned down by a metal lathe to bring them into an extruding shape with a typical selected outer diameter of between 3½ and 7 inches to a tolerance of 15,000ths of an inch. The ingots are then available for extrusion.

Extruding the metal matrix composite of the present invention first involves preheating the ingots in a resistance furnace for a minimum period of one hour at 555 degrees Centigrade. This is normally done in two steps. First the ingots are heated to 315 degrees Centigrade in a holding furnace and then heated to a higher temperature and held until the ingot temperature reaches 555 degrees Centigrade. The ingots are then loaded directly into a container or chamber from the furnace. The chamber temperature should preferably be 488 degrees Centigrade. The face pressure within the chamber depends upon the type of extrusion dimensions that are desired. Typically, the pressures used are 15–20% higher than extrusion pressures used for 6061 aluminum ingots. For example, for a 3½ inch outer diameter billet made of the metal matrix composite of the present invention, 3,500 psi peak (break out) pressure is typically used and results in an extruding pressure of about 3,000 psi. The speed of the extrusion could be an average of 15–30 feet per minute and the exit temperature should be 20 degrees Centigrade cooler than the container temperature. The speed of the ram used for the extrusion should run 3½ inches every minute on a typical 3½ inch outer diameter ingot.

Although the present invention may be extruded in conventional dies, it has been found that for maximum die insert life, a die bearing material made of titanium diboride is preferred. The titanium diboride die bearing material is preferably hot pressed and then electrodischarge machined to the appropriate size. A small amount of boron carbide may be used to increase the hardness of the die. Typically, the die is made of 99.5% pure titanium diboride in an amount equal to 92–98% by weight, the remaining fraction being 99.5% pure boron carbide having particulate sizes less than 10 microns. The hot press cycle for manufacture of the die bearing material is preferably done at 1,800 degrees Centigrade using a 3,500 psi pressure with the pressure and temperature maintained until a zero drop in ram travel is obtained.

The extruded metal matrix composite provides the greatest benefit if it is heat treated using a T6-type heat treatment which comprises two hours at 530 degrees Centigrade with a cold water quench and an artificial aging at 177 degrees Centigrade for ten hours. All welding, however, has to be accomplished before heat treatment is applied. Unlike other metal matrix composites which contain silicon carbide and aluminum oxide where welding can be a problem, the metal matrix composite of the present invention is readily weldable. Other metal matrix composites form aluminum carbides as brittle components of a weld. Aluminum carbides are formed from the chemical reaction of aluminum and silicon carbide. Because of the surface area of the aluminum oxide particulates and metal matrices, clumping and dewetting occurs. These brittle components and particulates clump together thereby greatly decreasing the strength of a weld body. The metal matrix composite of the present invention does not have these problems. The coated boron carbide particulates tend to flux and move into the weld pool which creates a very strong weld joint. Because boron carbide particulates have a melting point of 2,450 degrees Centigrade, the boron carbide is chemically inert at aluminum processing temperatures.

Depending upon the ratio of boron carbide to aluminum and also depending upon the particular aluminum alloy used as the base material metal, the resulting material has a density of less than 2.70 grams per cubic centimeter which is lower than aluminum 6061. One formulation has a density of 2.52 grams per cubic centimeter. The resulting material also has a tensile strength of 62–108 kpsi, a yield strength of 58–97 kpsi, a modulus of elasticity of from 14.25–14.50 Mpsi, and is extremely fracture resistant and more predictable than other composites. Furthermore, the resulting material of the present invention has a hardness which is comparable to that of titanium and chromoly steel, but a density which is roughly a third of steel and roughly 60% of titanium.

Two advantageous products made from the metal matrix composites of the invention are bicycle frames and golf club heads. Bicycle frames made from extruded and welded tubing of the inventive material are lighter, stiffer, and stronger than comparable bicycle frames made of more conventional materials such as aluminum, steel, or titanium. In golf clubs, the lower density of the inventive material allows for thicker walled heads, better weight distribution, balance, and aerodynamics. Furthermore, a larger "sweet spot" is possible in tournament legal clubs.

Some particular exemplary applications are as follows:

1) Discs used as substrates for hard drives in computer systems.

2) Extruded structural components for various transportation vehicles—e.g. bicycles, motorcycles, aircraft, military vehicles—including frames, interior floors and panels, handle bars, propulsion structures, flight control systems, fuel management systems and landing gear.

3) Cast structural components and auxiliary parts for various transportation vehicles—bicycles, motorcycles, aircraft, and auto waterpumps, bicycle cranks, disc brakes, and landing gear.

4) Housings for batteries where light weight and corrosion resistance are important.

5) Housings for electronic "boxes" for numerous applications where weight, high impact strength, and low thermal expansion are considerations—e.g., stamped casings for cellular phones, notebook computers, portable electronics.

6) Extruded structural parts of sporting goods equipment, e.g., tennis rackets, badminton rackets, baseball bats, arrows, golf club shafts, eyeglasses, oars, hockey sticks, billiard cues, ping pong paddles, lacrosse sticks, racquet ball rackets and basketball stanchions.

7) Cast sporting goods components such as golf club heads, archery equipment, ball throwing equipment, camping equipment, exercise equipment, fishing reels, hiking and mountaineering accessories, skate trucks, locks, optical frames, rowing equipment, water skis and snowboards.

8) Spray coatings for thermal, abrasive, and other forms of protection.

9) Nuclear shielding applications.

10) Internal combustion engine components—engine blocks, pistons, rods, valves, camshafts, and crankshafts.

11) Marine applications for extruded and cast material—spars, turnbuckles, propellers, and portholes.

12) Robotics applications for extruded and cast material where light weight, strength and fatigue resistance are critical.

13) Substrates for high power electronic components.

14) Structures for carts, amusement rides, ski lifts, elevators, escalators, moving sidewalks, trams and other general people moving purposes.

15) Gourmet cookware, knives, and other consumer niche markets.

16) Casings and parts for toys.

17) Armor for vehicles, personal security.

18) High pressure containers; e.g., gas storage, power transformers.

19) Casings and bits for down-hole drilling assemblies in oil prospecting.

20) Large structures where weight and toughness is important—e.g., inner hulls for oil tanker ships.

21) Portable tools of all kinds, for industrial, commercial, medical and construction use, where light weight and toughness are paramount.

22) Medical applications—e.g., prosthesis, braces, medical instruments and tools, where strength and light weight are important.

23) Dental applications—drill bits.

24) Transducers—bases and other parts of sensors for temperature and other parameters.

25) Channels, attenuators, combiners and other components of microwave networks and transmission systems.

26) Structures for spacecraft and satellites where low thermal expansion and light weight are key features.

Although described herein are preferred embodiments of the material composition and method of fabrication of the present invention, the invention may have other applications and embodiments. Such modifications as are within the knowledge of those skilled in the art are encompassed by the spirit and scope of the invention.

I claim:

1. A metal matrix composite for structural applications, comprising:

a base material metal and boron carbide in a ratio of approximately between 3 and 10 to 1 by weight, the boron carbide being substantially homogeneously distributed among the metal, forming close grain boundaries therewith; and less than about 3.0% by weight of at least one metal having an intermetallic phase temperature lower than the melting point of the base material metal, the at least one metal providing a chelating opportunity for the base material metal, wherein the composite is extrudable and weldable, and the composite undergoes yield by plastic deformation without brittle fracture.

2. A metal matrix composite comprising, a base material metal and boron carbide in a ratio of approximately between 3 and 10 to 1 by weight, the boron carbide being substantially homogeneously distributed among the metal, forming close grain boundaries therewith, wherein the base material metal is selected from the group consisting essentially of magnesium and alloys of magnesium; and less than about 3.0% by weight of at least one metal having an intermetallic phase temperature lower than the melting point of the base material metal, the at least one metal providing a chelating opportunity for the base material metal, wherein the composite is extrudable and weldable.

3. The composite recited in claim 1, wherein the base material metal is selected from the group consisting essentially of aluminum, titanium, and alloys thereof.

4. The composite recited in claim 1, wherein the composite has a density of about 2.5 grams per cubic centimeter.

5. The composite recited in claim 1, wherein the composite has a tensile strength of about 62–108 kpsi.

6. The composite recited in claim 1, wherein the composite has a yield strength of about 58–97 kpsi.

7. The composite recited in claim 1, wherein the composite has a modulus of elasticity of about 14–15 Mpsi.

8. The composite recited in claim 1, wherein the base material metal is aluminum alloy 6061, boron carbide is present in a ratio of approximately 5 to 1 by weight, and the composite has a tensile strength of about 65 kpsi and a yield strength of about 60 kpsi.

9. The composite recited in claim 1, wherein the base material metal is aluminum alloy 6061, boron carbide is present in a ratio of approximately 4 to 1 by weight, and the composite has a tensile strength of about 72 kpsi and a yield strength of about 63 kpsi.

10. The composite recited in claim 1, wherein the base material metal is aluminum alloy 6061, boron carbide is present in a ratio of approximately 3 to 1 by weight, and the composite has a tensile strength of about 62 kpsi and a yield strength of about 58 kpsi.

11. The composite recited in claim 1, wherein the base material metal is aluminum alloy 7091, boron carbide is present in a ratio of approximately 5 to 1 by weight, and the composite has a tensile strength of about 99 kpsi and a yield strength of about 89 kpsi.

12. The composite recited in claim 1, wherein the base material metal is aluminum alloy 7091, boron carbide is present in a ratio of approximately 3 to 1 by weight, and the composite has a tensile strength of about 108 kpsi and a yield strength of about 96 kpsi.

13. An extrudable and weldable metal matrix composite for structural applications, formed by the process of:
   a) blending powders of a base material metal, boron carbide, and at least one metal having an intermetallic phase temperature below the melting point of the base material metal, wherein the boron carbide constitutes about 10–30% of the powders by weight and the at least one metal constitutes less than about 3.0% of the powders by weight, the at least one metal providing a chelating opportunity for the base material metal;
   b) degassing the blended powders;
   c) isopressing the blended powders at a pressure of at least 65,000 psi;
   d) heating the isopressed powders up to at least 625 degrees Centigrade over a selected period of time;
   e) configuring the isopressed and sintered powders to form a composite material;
   f) heat treating the composite material to form a composite which yields by plastic deformation without brittle fracture; and
   g) at least one of extruding the composite material and welding the composite material.

14. A metal matrix composite formed by the process of:
   a) blending powders of a base material metal, boron carbide, and at least one metal having an intermetallic phase temperature below the melting point of the base material metal, wherein the boron carbide constitutes about 10–30% of the powders by weight and the at least one metal constitutes less than about 3.0% of the powders by weight, the at least one metal additive providing a chelating opportunity for the base material metal, wherein the base material metal is selected from the group consisting essentially of magnesium and alloys of magnesium;
   b) degassing the blended powders;
   c) isopressing the blended powders at a pressure of at least 65,000 psi;
   d) heating the isopressed powders up to at least 625 degrees Centigrade over a selected period of time;
   e) configuring the isopressed and sintered powders to a desired shape; and
   f) heat treating the desired shape.

15. The metal matrix composite recited in claim 13, wherein the base material metal is selected from the group consisting essentially of aluminum, titanium, and alloys thereof.

* * * * *